United States Patent [19]

Hansmann et al.

[11] Patent Number: 5,712,394

[45] Date of Patent: Jan. 27, 1998

[54] PROCESS FOR PREPARING 2,4,6-TRICHLOROPYRIMIDINE

[75] Inventors: Wilfried Hansmann, Leverkusen; Stefan Ehrenberg, Frankfurt; Frank-Michael Stöhr, Odenthal, all of Germany

[73] Assignee: Bayer Aktiengesellschaft, Leverkusen, Germany

[21] Appl. No.: 656,746

[22] Filed: Jun. 3, 1996

[30] Foreign Application Priority Data

Jun. 9, 1995 [DE] Germany .................. 195 21 036.0

[51] Int. Cl.$^6$ ................................ C07D 239/30
[52] U.S. Cl. ........................................... 544/334
[58] Field of Search ................................ 544/334

[56] References Cited

PUBLICATIONS

J. Baddiley, et al., J. Chem. Soc., pp. 678–679, (1944).
H. Brederick, et al., Chem. Ber., vol. 92, pp. 2937–2943, (1959).
M.M. Robinson, J. Am. Chem. Soc., vol. 80, pp. 5481–5483, (1958).

*Primary Examiner*—John M. Ford
*Attorney, Agent, or Firm*—Sprung Kramer Schaefer & Briscoe

[57] ABSTRACT

Process for preparing 2,4,6-trichloropyrimidine, characterized in that, in a first reaction step, barbituric acid is reacted, optionally in the presence of a catalyst, with phosphorus oxychloride and subsequently, in a second reaction step, with phosphorus pentachloride or with reactants forming the latter, in particular phosphorus trichloride and chlorine.

10 Claims, No Drawings

PROCESS FOR PREPARING 2,4,6-TRICHLOROPYRIMIDINE

The present invention relates to a new process for preparing 2,4,6-trichloropyrimidine.

2,4,6-Trichloropyrimidine can be prepared by a process as described in Chem. Ber. 92 (1959) 2937 by reacting barbituric acid with phosphorus oxychloride ($POCl_3$) in the presence of dimethylaniline. The 2,4,6-trichloropyrimidine thus obtained is worked up in aqueous medium. The yield, based on barbituric acid, is 85% of theory. However, this process is associated with disadvantages. Thus, for example, the aqueous work-up of the reaction mixture containing 2,4,6-trichloropyrimidine is inconvenient for a large-scale process since extraction of the aqueous phase is generally required. In addition, the aqueous work-up results in large amounts of wastewater. Furthermore, a large mount of the tertiary amine is required in the process (about 1.8 mol per mol of barbituric acid).

If a smaller amount of dimethylaniline is used, as in the process of J. Baddiley et at. J. Chem. Soc. 1944, 678 (about 0.8 mol per mol of barbituric acid), the yield drops to 59%. If the 2,4,6-trichloropyrimidine is required as an anhydrous starting material for further reactions, a subsequent complicated dewatering step is unavoidable. These disadvantages, as well as low yield, also apply when using phenylphosphonic dichloride in place of phosphorus oxychloride as per the process described in M. M. Robinson, J. Am. Chem. Soc. 80 (1958) 5481.

A process has been found for preparing 2,4,6-trichloropyrimidine which is characterized in that, in a first reaction step, barbituric add is reacted, optionally in the presence of a catalyst, with phosphorus oxychloride ($POCl_3$) and subsequently, in a second reaction step, with phosphorus pentachloride ($PCl_5$) or with reactants forming the latter, in particular phosphorus trichloride ($PCl_3$) and chlorine. It is advantageous if the phosphorus oxychloride formed and the unreacted phosphorus oxychloride and the 2,4,6-trichloropyrimidine are subsequently separated off from the reaction mixture, in particular by distillation.

The phosphorus oxychloride separated off, in particular by distillation, can, for example, be reused in the process of the invention.

In a preferred embodiment of the process of the invention, the first reaction step is carried out at a temperature of from 70° to 115° C., in particular at the boiling point of the reaction mixture at atmospheric pressure, and the second reaction step is carried out at a temperature of from 80° to 120° C., preferably likewise at the boiling point of the reaction mixture at atmospheric pressure.

The phosphorus oxychloride is preferably used in an amount of from 3 to 6 mol, in particular from 5 to 6 mol, based on 1 mol of barbituric acid.

Although it is possible to use amounts of phosphorus oxychloride which are greater than 6 mol or smaller than the 3 mol stoichiometrically required for complete reaction, based on 1 mol of barbituric acid, they offer no particular advantage.

Phosphorus oxychloride preferably assumes the function of a solvent, so that the process of the invention can preferably be carried out without additional solvents.

However, the respective reaction steps can also proceed in the presence of an inert solvent. It is also advantageous to carry out the process in the absence of water. Hydrogen chloride formed is evolved both in the first reaction step and in the second reaction step, preferably in the second reaction step, and this can, for example, be removed from the waste air by means of a scrubber.

Suitable catalysts which may optionally be present in the first reaction step are, for example, organic bases such as tertiary amines such as triethylamine, tripropylamine, tri-n-butylamine, dimethylaniline, diethylaniline, N,N-diethylmethylaniline, N-ethyl-diisopropylamine, trioctylamine, triisobutylamine, 1,8-bis(dimethylamino)-naphthalene, N,N-dimethyl-p-toluidine or the like, also N-substituted carboxamides and sulphonamides or N,N-disubstituted carboxamides and sulphonamides such as N,N-dimethylformamide, N,N-diethylformamide, N,N-dimethylacetamide, N,N-diethylacetamide, N-formylpiperidine, tetramethylurea, 1-alkyl-2-pyrrolidones such as 1-methyl-2-pyrrolidone (NMP), 1-octyl-2-pyrrolidone or 1-dodecyl-2-pyrrolidone, dibutyl-formamide and methyl-stearyl-formamide and also basic heterocycles such as pyridine, 2-methylpyridine, 3-methylpyridine, 4-methylpyridine, 2-ethylpyridine, 4-ethylpyridine, 2,4-dimethylpyridine, 2,6-dimethylpyridine, 3,5-dimethylpyridine, 5-ethyl-2-methylpyridine, 2,4,6-trimethylpyridine, 4-(dimethylamino)-pyridine, 4-(1-pyrrolidinyl)-pyridine and quinoline; naturally, it is also possible to use mixtures of the specified catalysts.

Catalysts optionally used are preferably used in an mount of less than 0.5 mol, in particular less than 0.1 mol, per mol of barbituric acid, with amounts larger than 0.5 mol per mol of barbituric acid offering no particular advantage. In the second reaction step, reaction occurs with preferably from 2.5 to 3.5 mol of phosphorus pentachloride or reactants forming the latter, in particular from 2.5 to 3.5 mol of phosphorus trichloride and from 2.5 to 3.5 mol of chlorine, per mol of barbituric acid. The reaction of the process of the invention proceeds particularly favourably when phosphorus trichloride and chlorine are used in stoichiometric mounts; i.e. 3 mol of chlorine and 3 mol of phosphorus trichloride are used per mol of barbituric acid. It is advantageous to add the phosphorus trichloride completely or partially before or simultaneously with the chlorine. Phosphorus trichloride and chlorine are preferably metered simultaneously into the reaction mixture. Chlorine gas is here preferably passed directly into the reaction mixture through a gas inlet tube. It is particularly advantageous if no excess of chlorine is present during the reaction.

In a further preferred embodiment of the process of the invention, after the second reaction step is complete, the phosphorus oxychloride formed and the unreacted phosphorus oxychloride are reacted in the reaction mixture, i.e. without having been isolated from the reaction mixture, with barbituric acid, optionally with renewed addition of catalyst, followed by the reaction with phosphorus pentachloride or reactants forming the latter, in particular phosphorus trichloride and chlorine, and this two-stage reaction sequence is repeated a plurality of times if desired.

The reaction conditions of these two reaction steps which may optionally be carried out a plurality of times in succession correspond to the process conditions according to the invention.

This procedure can be repeated a plurality of times, with the number of sequences and the amount of product thus prepared generally being guided by the dimensions of the reactor. After the last sequence, the reaction mixture is worked up according to the invention.

The yield of 2,4,6-trichloropyrimidine which is obtained by the process of the invention is generally from 80 to 95% of theory, based on barbituric acid. The 2,4,6-trichloropyrimidine thus obtained is essentially free of 2,4,5,6-tetrachloropyrimidine and also of water. Chlorination at the 5 position of the pyrimidine was not observed under the process conditions according to the invention. The process of the invention offers a number of advantages in comparison with the processes known hitherto. Apart from a higher yield, the 2,4,6-trichloropyrimidine can be isolated in very pure form from the reaction mixture by distillation in a technically extraordinarily simple manner. Furthermore, in the case of a preferably nonaqueous work-up, wastewater is not obtained at all.

2,4,6-Trichloropyrimidine is known as an important intermediate for the preparation of reactive dyes and as starting material for the preparation of further important pyrimidine derivatives such as 2,4,6-trifluoropyrimidine.

EXAMPLES

Example 1

500 ml (5.5 mol) of phosphorus oxychloride were placed in a 2l four-necked flask and 128.1 g (1 mol) of barbituric acid were introduced while stirring. 2.5 ml (0.026 mol) of 1-methyl-2-pyrrolidone (NMP) were then added, the mixture was stirred and boiled under reflux for 2 hours. The reaction mixture was subsequently cooled to 80° C. and admixed with 25 ml (0.29 mol) of phosphorus trichloride. Subsequently, 250 ml (2.86 mol) of phosphorus trichloride and 213.0 g (3 mol) of chlorine were added simultaneously over a period of 4 hours. Care was taken to ensure that no excess of chlorine was present during the reaction and as soon as chlorine gas was visible in the condenser the chlorine feed was throttled back. The reaction mixture was continually maintained under gentle reflux. After addition was complete, the reaction mixture was maintained at boiling point at about 11° C. for at least 1 hour until a clear solution was obtained. Subsequently, the major part of the phosphorus oxychloride was first distilled off via a column at atmospheric pressure and 110°–140° C. bottom temperature and the remainder was then distilled off at 20 mbar and 40°–80° C. bottom temperature. 172.0 g (93.8% of theory, based on barbituric acid) of 2,4,6-trichloropyrimidine were then distilled off at about 95° C. and 20 mbar, the bottom temperature being increased from 100° C. to 160° C. Purity: 99% (determined by gas chromatography (GC))

Example 2

128.1 g (1 mol) of barbituric acid and 500 ml (5.5 mol) of phosphorus oxychloride were boiled under reflux for 4 hours. The pale yellow suspension was subsequently treated simultaneously with 270 ml (3.1 mol) of phosphorus trichloride and 213 g (3 mol) of chlorine over a period of 4 hours at the boiling point. During the addition, care was taken to ensure, as already described in Example 1, that no excess of chlorine was present during the reaction. After addition was complete, the reaction mixture was maintained at reflux for a further hour, and the phosphorus oxychloride was subsequently distilled off. The 2,4,6-trichloropyrimidine was then distilled off in a water pump vacuum as described in Example 1. Yield: 148 g of 2,4,6-trichloropyrimidine (81% of theory, based on barbituric acid) which is free of 2,4,5,6-tetrachloropyrimidine (determined by GC).

Example 3

25.9 g (0.2 mol) of barbituric acid, 101.4 ml (1.1 mol) of phosphorus oxychloride and 0.5 ml (0.005 mol) of 1-methyl-2-pyrrolidone (NMP) were boiled under reflux for 2 hours. While boiling, 54.5 ml (0.62 mol) of PCl$_3$ and 43.0 g (0.61 mol) of chlorine were then added over a period of 4 hours in such a way that no excess of chlorine was present. The mixture was stirred further for 1 hour while boiling.

40 g (0.31 mol) of barbituric acid and 0.8 ml (0.008 mol) of NMP were then added to the reaction mixture. The reaction mixture was maintained at reflux for 2 hours. While boiling gently, 84.6 ml (0.97 mol) of phosphorus trichloride and 66.4 g (0.94 mol) of chlorine were then added simultaneously over a period of 4 hours in such a way that no excess of chlorine was present. After stirring further for 1 hour at the boiling point, 61.7 g (0.48 mol) of barbituric acid and 1.2 ml (0.012 mol) of NMP were added to the reaction mixture. The reaction mixture was maintained at boiling point for 2 hours. While boiling gently, 130.1 ml (1.49 mol) of phosphorus trichloride and 102.7 g (1.45 mol) of chlorine were then added over a period of 4 hours in such a way that an excess of chlorine was never present. After stirring further for 1 hour at the boiling point, the phosphorus oxychloride was distilled off.

The 2,4,6-trichloropyrimidine was then distilled in a waterpump vacuum. Yield: 149 g (81% of theory, based on barbituric acid) Purity: 98% (determined by GC).

Example 4

A mixture of
33.50 kg (218.5 mol) of phosphorus oxychloride
5.12 kg (40.0 mol) of barbituric acid
1.56 kg (11.4 mol) of phosphorus trichloride and
0.30 kg (1.6 mol) of tri-n-butylamine was boiled under reflux for 2 hours while stirring.

The mixture was then cooled to 80° C. and
15.60 kg (114 mol) of phosphorus trichloride and
8.51 kg (120 mol) of chlorine were then added simultaneously to the reaction mixture over a period of 4 hours, with the heat of reaction being removed by boiling under reflux (temperature of the mixture: 100°–107° C.).

After the introduction of chlorine was complete, the mixture was heated under reflux until HCl evolution had ceased.

The subsequent distillative work-up gave
53.20 kg of phosphorus oxychloride and
6.95 kg of 2,4,6-trichloropyrimidine having a purity of 97.6%, which corresponds to a yield of 92.4% of theory, based on barbituric acid.

Example 5

500 ml (5.5 mol) of phosphorus oxychloride were placed in a 2l four-necked flask and 128.1 g (1 mol) of barbituric acid were introduced while stirring. 2.5 ml (0.026 mol) of 1-methyl-2-pyrrolidone (NMP) were then added. The reaction mixture was subsequently stirred for 7 hours at 80° C. and then admixed with 262 ml (3 mol) of phosphorus trichloride. Subsequently, 213.0 g (3 mol) of chlorine were added over a period of 4 hours. Care was taken to ensure that no excess of chlorine was present during the reaction and as soon as chlorine gas was visible in the condenser the chlorine feed was throttled back. The reaction mixture was continually maintained under gentle reflux. After addition was complete, the reaction mixture was maintained at the boiling point at about 110° C. for at least 1 hour until a clear solution had been obtained. Subsequently, the major part of the phosphorus oxychloride was first distilled off via a column at atmospheric pressure and 110°–140° C. bottom temperature and the remainder was then distilled off at 20 mbar and 40°–80° C. bottom temperature. 172.0 g (93.8% of theory, based on barbituric acid) of 2,4,6-trichloropyrimidine were then distilled off at about 95° C. and 20 mbar, with the bottom temperature being increased from 100° C. to 160° C.

Purity: 99% (determined by gas chromatography (GC)).

We claim:

1. Process for preparing 2,4,6-trichloropyrimidine, wherein in a first reaction step, barbituric acid is reacted, with phosphorus oxychloride whereby the reaction is carried out in the presence or absence of a catalyst and subsequently, in a second reaction step, with phosphorus pentachloride or with reactants forming the latter.

2. Process according to claim 1, wherein the reactants forming phosphorus pentachloride are phosphorus trichloride and chlorine.

3. Process according to claim 1, wherein the first reaction step is carried out at a temperature of from 70° to 115° C. and the second reaction step is carried out at a temperature of from 80° to 120° C.

4. Process according to claim 1, wherein the second reaction step is carried out at the boiling point of the respective reaction mixture at atmospheric pressure.

5. Process according to claim 2, wherein in the second reaction step the phosphorus trichloride is added completely or partially before or simultaneously with the chlorine.

6. Process according to claim 5, wherein for the reaction of the second reaction step, phosphorus trichloride and chlorine are metered simultaneously into the reaction mixture.

7. Process according to claim 1, wherein tertiary mines, N-substituted carboxamides and sulphonamides or N,N-disubstituted carboxamides and sulphonamides, or basic heterocycles are used as catalyst.

8. Process according to claim 1, wherein triethylamine, tributylamine, N,N-dimethylformamide or 1-methyl-2-pyrrolidone are used as catalyst.

9. Process according to claim 1, wherein from 2.5 to 3.5 mol, of phosphorus trichloride and from 2.5 to 3.5 mol. of chlorine are used per mol of barbituric acid.

10. Process according to claim 1, wherein after the second reaction step is complete, the phosphorus oxychloride formed and the unreacted phosphorus oxychloride are reacted in the reaction mixture with barbituric acid, optionally with renewed addition of catalyst, followed by the reaction with phosphorus pentachloride or reactants forming the latter, and this two-stage reaction sequence is repeated a plurality of times if desired.

* * * * *

UNITED STATES PATENT AND TRADEMARK OFFICE
CERTIFICATE OF CORRECTION

PATENT NO : 5,712,394
DATED : January 27, 1998
INVENTOR(S) : Wilfried HANSMANN, et al.

It is certified that error appears in the above-identified patent and that said Letters Patent is hereby corrected as shown below:

Title Page
After "[56] References Cited" insert
--U.S. PATENT DOCUMENTS:
3,714,164, 1/1973, Guido, 260/251

FOREIGN PATENT DOCUMENTS 373,045, 12/1963, Switzerland
221,736, 5/1985, Germany
697,406, 2/1996, European Pat. Office
101,561, 2/1984, European Pat. Office
1,933,784, 1/1971, Germany--

Column 6, line 1,
Delete "mines" and substitute --amines--

Signed and Sealed this

Twenty-first Day of November, 2000

Attest:

Q. TODD DICKINSON

*Attesting Officer*      *Director of Patents and Trademarks*